(12) United States Patent
Zeichner et al.

(10) Patent No.: US 8,497,251 B2
(45) Date of Patent: *Jul. 30, 2013

(54) METHODS AND COMPOSITIONS FOR TREATING HIV INFECTION

(75) Inventors: Steven L. Zeichner, Bethesda, MD (US); Guerau Fernandez, Silver Spring, MD (US)

(73) Assignee: Children's Research Institute, Children's National Medical Center, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,260

(22) Filed: May 29, 2012

(65) Prior Publication Data

US 2012/0263782 A1    Oct. 18, 2012

Related U.S. Application Data

(63) Continuation of application No. 12/687,255, filed on Jan. 14, 2010, now Pat. No. 8,211,866.

(60) Provisional application No. 61/193,972, filed on Jan. 14, 2009.

(51) Int. Cl.
*C07H 21/04* (2006.01)

(52) U.S. Cl.
USPC .......... 514/44; 536/24.5; 536/24.31; 536/24.1

(58) Field of Classification Search
None
See application file for complete search history.

(56) References Cited

PUBLICATIONS

Hayden, Matthew S., et al., "Shared Principles in NFκB Signaling", Cell, (2008), pp. 344-362, vol. 132.
Tiscornia, Gustavo, et al., "A general method for gene knockdown in mice by using lentiviral vectors expressing small . . . ", PNAS, (2003), pp. 1844-1848, vol. 100, No. 4.
Peer, Dan, et al., "Selective gene silencing in activated leukocytes by targeting siRNAs to the integrin lymphocyte function . . . " PNAS, (2001), pp. 4095-4100, vol. 104, No. 10.
Banerjea, Akhil, et al., "Inhibition of HIV-1 by Lentiviral Vector-Transduced siRNAs in T Lymphocytes . . . " Molecular Therapy, (2003), pp. 62-71, vol. 8, No. 1.
Li, Mingjie, et al., Lentiviral Vector Delivery of siRNA and shRNA Encoding Genes into Cultured and Primary Hematopoietic Cells, (2008), pp. 287-299, vol. 433, No. 1.
Kumar, Priti, et al., "T Cell-Specific siRNA Delivery Suppresses HIV-1 Infection in Humanized Mice", Cell 134, (2008), pp. 577-586.
Lee, Nan Sook., et al., "Expression of small interfering RNAs targeted against HIV-1 rev transcripts in human cells", Nature Biotechnology, (2002), pp. 500-505, vol. 19.
Tyagi, Mudit, et al., "CBF-1 promotes transcriptional silencing during the establishment of HIV-1 latency", The EMBO Journal, (2007), pp. 4985-4995, vol. 26, No. 24.
Lafeuillade, Alan, et al., "The Search for a Cure for Persistent HIV Reservoirs", AIDS, (Rev. 2011), pp. 63-66, vol. 13.
Lafeuillade, Alan, et al., "Pilot Study of a Combination of Highly Active Antiretroviral Therapy and Cytokines to Induce HIV-Remission", Journal of Acquired Immune Deficiency Syndromes, (2001), pp. 44-55, vol. 26.
Van Praag, R.M.E., et al., "OKT3 and IL-2 Treatment for Purging of the Latent HIV-1 Reservoir in Vivio Results in Selective Long-Lasting CD4+ T Cell Depletion", Journal of Clinical Immunology, (2001), pp. 218-226, vol. 21, No. 3.
Prins, Jan M., et al., "Immuno-activation with anti-CD3 and recombinant human IL-2 in HIV-1-infected patients on potent antiretroviral therapy", AIDS, (1999), pp. 2405-2410, vol. 13.
Matalon, Shay., et al., "Histone Deacetylase Inhibitors for Purging HIV-1 from latent Reservoir", Mol Med, (2011), pp. 466-472, vol. 17, No. 5-6.
Sui, Guangchao, et al., "A DNA vector-based RNAi technology to suppress gene expression in mammalian cells", PNAS, (2002), pp. 5515-5520, vol. 99, No. 8.
Siliciano, Janet D., of al., "A long-term latent reservoir for HIV-1: discovery and clinical implications", Journal of Antimicrobial Chemotherapy, (2004), pp. 6-9, vol. 54.

*Primary Examiner* — Kimberly Chong
(74) *Attorney, Agent, or Firm* — Michael Ye; Andrews Kurth, LLP

(57) ABSTRACT

A method for treating latent HIV infection is disclosed. The method includes administering to a subject in need of such treatment an effective amount of an anti-IκBα agent, an anti-IκBε agent or both; and administering to the subject an effective amount of an antiviral agent. A pharmaceutical composition for treating latent HIV infection is also disclosed.

20 Claims, 4 Drawing Sheets

METHODS AND COMPOSITIONS FOR TREATING HIV INFECTION

RELEVANT APPLICATIONS

This application is a Continuation of U.S. patent application Ser. No. 12/687,255 filed Jan. 14, 2010, now allowed, which claims priority of U.S. Provisional Application Ser. No. 61/193,972, filed on Jan. 14, 2009. The entirety of both applications is incorporated herein by reference.

FIELD

The technical field is medical treatment and, in particular, treatment for HIV infection, the persistence of HIV infection, and the existence of long-lived reservoirs of HIV-infected cells.

BACKGROUND

One of the barriers to HIV eradication is viral latency. For example, widely used highly active antiretroviral therapy (HAART) is only effective in reducing virus load in the blood and slow down the development of AIDS, but cannot completely eradicate HIV from an infected individual. Viral reservoirs established early during the infection remain unaffected by the anti-retroviral therapy for a long time and are able to reinitiate systemic infection upon interruption of the treatment. Therapeutic targeting of viral latency will require a better understanding of the basic mechanisms underlying the establishment and long-term maintenance of HIV in resting memory CD4 T cells, the most prominent reservoir of transcriptionally silent provirus.

SUMMARY

A method for treating HIV infection is disclosed. The method includes: administering to a subject in need of such treatment an effective amount of an anti-I$\kappa$B$\alpha$ agent, an anti-I$\kappa$B$\epsilon$ agent or both; and administering to said subject an effective amount of an antiviral agent.

Also disclosed is a pharmaceutical composition for treating latent HIV infection. The pharmaceutical composition contains (1) an anti-I$\kappa$B$\alpha$ agent, an anti-I$\kappa$B$\epsilon$ agent or both; and (2) a pharmaceutically acceptable carrier.

BRIEF DESCRIPTION OF DRAWINGS

The detailed description will refer to the following drawings, wherein like numerals refer to like elements, and wherein.

DETAILED DESCRIPTION

Figure 1:
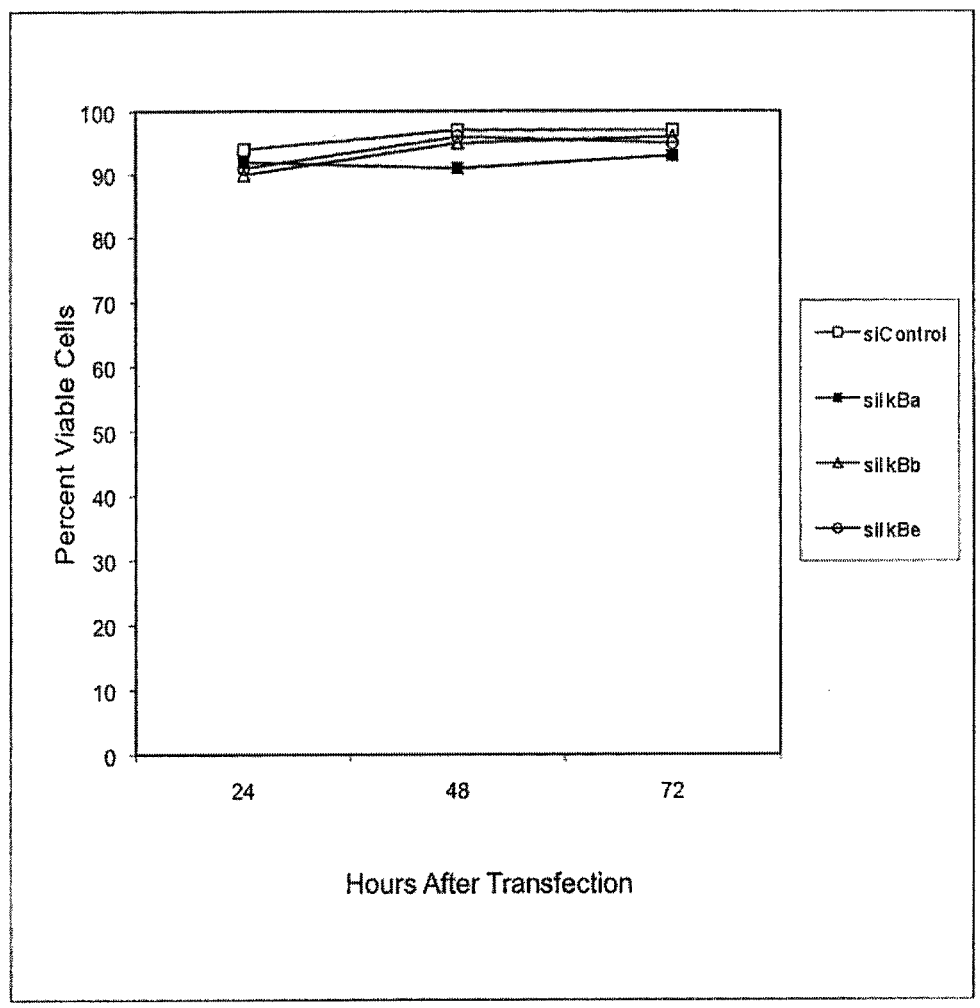
FIG. 1 is a diagram showing cell viability after transfection with siRNAs targeting I$\kappa$B$\alpha$, I$\kappa$B$\beta$, and I$\kappa$B$\epsilon$. Cells (U1) were transfected with the siRNAs against the 3 major I$\kappa$B species and with a non-specific control siRNA (data shown from 1000 nM transfections). Little cellular toxicity was observed over the course of the experiment.

This description is intended to be read in connection with the accompanying drawings, which are to be considered part of the entire written description of this invention. The drawings are not necessarily to scale and certain features of the invention may be shown exaggerated in scale or in somewhat schematic form in the interest of clarity and conciseness.

As used herein the specification, "a" or "an" may mean one or more. As used herein in the claim(s), when used in conjunction with the word "comprising", the words "a" or "an" may mean one or more than one.

The present invention is developed based on the observation that selective knockdown of a single I$\kappa$B species (e.g., I$\kappa$B$\alpha$ or I$\kappa$B$\epsilon$) is sufficient to activate HIV from latency. I$\kappa$Bs are a family of related proteins that inhibit the activity of NF-$\kappa$B (nuclear factor kappa-light-chain-enhancer of activated B cells; which includes several different family members, all of which are encompassed by this application) which plays a key role in regulating the immune response to viral infection and other inducible responses of cells. The IkB family includes 3 typical IkB proteins, IkBA, IkBB, and IkBE, and their precursor proteins, p100 and p105, and two atypical IkB proteins, Bcl-3 and I$\kappa$B$\zeta$ (See, e.g., Hayden and Ghosh, Cell 2008; 132:344-62).

Method for Treating HIV Latency

One aspect of the present invention relates to a method for treating latent HIV infection. The method includes: administering to a subject in need of such treatment an effective amount of an anti-I$\kappa$B-$\alpha$ agent, an anti-I$\kappa$B-$\epsilon$ agent or both; and administering to said subject an effective amount of an antiviral agent.

In certain embodiments, the anti-I$\kappa$B-$\alpha$ agent and/or anti-I$\kappa$B-$\epsilon$ agent are designed to specifically target cells that are capable of harboring dormant HIV, such as lymphocytes, neural cells and neural-related cells (such as astrocytes), and cells of the reproductive system. The cell- or tissue-specific targeting may be achieved by conjugating the anti-I$\kappa$B-$\alpha$ agent and/or anti-I$\kappa$B-$\epsilon$ agent to antibodies (such as single chain antibodies (scFvs) against cell/tissue specific surface antigens, by using tissue-specific expression systems (e.g., expression systems with lymphocyte-specific promoters), by packaging the anti-I$\kappa$B agents in delivery systems, such as lipid micelles or microspheres that have receptors or other targeting ability for the cells of interest, by complexing the anti-I$\kappa$B agents with ligands for receptors on the cells of interest.

The term "latent HIV infection," as used herein, refers to the cellular latency of HIV infection (as in contrast to the clinical latency of HIV infection), i.e., the dormancy of HIV in resting memory CD4 T cells and other cells, including but not limited to monocyte/macrophages, neural cells (including gial cells and astrocytes), and cells of the reproductive system. Latency ends when the virus starts to actively replicates.

The term "anti-IκBα agent," as used herein, refers to any agent that is capable of reducing the level of IκBα gene expression or a biological activity of the IκBα protein. Similarly, the term "anti-IκBε agent" refers to any agent that is capable of reducing the level of IκBε gene expression or a biological activity of the IκB-ε protein. The term "gene expression," as used herein, refers to the process of transcription of mRNA from a coding sequence, translation of mRNA into a polypeptide, and post-translational modifications such as phosphorylation and glycosylation. A person of ordinary skill in the art would understand that an anti-IκBα agent may also have anti-IκBα activity and vice versa, an anti-IκBε agent may also have anti-IκBα activity. Examples of anti-IκBα and anti-IκBε agents include, but are not limited to, iRNA agents, antisense RNA, vectors expressing iRNA agents, or antisense RNA, PNA, anti-IκBα antibodies and anti-IκBε antibodies, small molecules that target IκB and IκB-NFκB interactions. These agents also include the agents attached to, complexed with, inserted into, or otherwise associated with the agents that target the anti-IκB agents to particular cell types or alter the metabolic properties, pharmacokinetic characteristics, or other characteristics of the anti-IκB agents.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA. The term "antibody", as used herein, is defined as an immunoglobulin that has specific binding sites to combine with an antigen.

The terms "PNA," as used herein, refers to "peptide polynucleotides" or polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. PNA oligomers can be synthesized using standard solid phase peptide synthesis protocols. PNAs can be used as antisense agents for sequence-specific modulation of a target gene expression.

The term "antibody", as used herein, is defined as an immunoglobulin that has specific binding sites to combine with an antigen. The term "antibody" is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, a humanized antibody and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), F(ab')$_2$, Fv fragment, diabody, linear antibody, single-chain antibody molecule, multispecific antibody, and/or other antigen binding sequences of an antibody.

The term "effective amount," as used herein, refers to an amount effective, at dosages and for periods of time necessary, to achieve the desired result, e.g., sufficient to inhibit gene expression or protein activity of IκBα or IκBε or both to a desired level. The effective amount of anti-IκBα agent, or anti-IκBε agent, or both may vary according to factors such as the disease state, age, and weight of the subject, and the ability of the particular agent or agents to elicit a desired response in the subject. Dosage regimens may be adjusted to provide the optimum therapeutic response. An effective amount is also one in which any toxic or detrimental effects (e.g., side effects) of the agent(s) are outweighed by the therapeutically beneficial effects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents which exhibit large therapeutic indices are preferred. While agents that exhibit toxic side effects may be used, care should be taken to design a delivery system that targets such compounds to the site of affected tissue in order to minimize potential damage to uninfected cells and, thereby, reduce side effects.

The term "antiviral agent," as used herein, refers to an agent (compound or biological) that is effective to inhibit the formation and/or replication of HIV in a mammal. Examples of antiviral agents include, but are not limited to, reverse transcriptase inhibitors such as azidothymidine (AZT), 2',3'-dideoxyinosine (DDI), 2',3'-didexoycytidine (DDC), didehydrothymidine (d4T), 2'-deoxy-3'-thiacytidine (3TC), abacavir succinate, and tenofovir disoproxil fumarate, nevirapine, delavirdine and efavirenz; protease inhibitors such as saquinavir, saquinavir mesylate, ritonavir, lopinavir, indinavir, nelfinavir mesylate, amprenavir, fosamprenavir, tipranavir, atazanavir, entry inhibitors such as maraviroc, vicriviroc, enfuvirtide, viral maturation inhibitors, agents targeting the expression of HIV genes, agents targeting key host cell genes and gene products involved in HIV replication, and other anti-HIV agents; iRNA agents, antisense RNA, vectors expressing iRNA agents or antisense RNA, PNA and antiviral antibodies.

Vectors Expressing iRNA Agents or Antisense RNA

Vectors expressing iRNA agents or antisense RNA include, but are not limited to non-viral vectors and viral vectors. Non-viral vectors typically include a plasmid having a circular double stranded DNA into which additional DNA segments can be introduced. The non-viral vector may be in the form of naked DNA, polycationic condensed DNA linked or unlinked to inactivated virus, ligand linked DNA, and liposome-DNA conjugates. Viral vectors include, but are not limited to, retrovirus, adenovirus, adeno-associated virus (AAV), herpesvirus, and alphavirus vectors. The viral vectors can also be astrovirus, coronavirus, orthomyxovirus, papovavirus, paramyxovirus, parvovirus, picornavirus, poxvirus, or togavirus vectors.

The non-viral and viral vectors also include one or more regulatory sequences operably linked to the polynucleotide being expressed. A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences. In one embodiment, the regulatory sequence comprises a lymphoid-specific promoter, such as promoters of T cell receptors and immunoglobulins.

siRNA as the Anti-IκBα Agent, Anti-IκBε Agent, or Antiviral Agent

In one embodiment, short interfering RNAs (siRNA) are used as an anti-IκBα agent, an anti-IκBε agent, or an antiviral agent. siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 nucleotides with symmetric 2 dinucleotide 3' overhangs. Using synthetic 21 bp siRNA duplexes (19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. Recent approaches used to selectively deliver RNAi to particular cell types include liposomal nanoparticles containing siRNAs incorporating antibodies against cell surface proteins, such as integrins (Peer D, et al. Proc Natl Acad Sci USA 2007, 104: 4095-100), AAV vector systems, lentiviral vector systems (including HIV-based lentiviral vector systems) (Tiscornia G, et al. Proc Natl Acad Sci USA 2003, 100:1844-1858, Banerjea A, et al. Mol Ther 2003, 8:62-71, Li M and Rossi J J. Methods Mol Biol 2008, 433:287-299). SiRNAs complexed with single chain antibodies (scFvs) against cell surface proteins modified to have a polylysine tail that binds the RNAs can be targeted specifically to lymphocytic cells bearing the surface antigen recognized by the scFvs (Kumar P, et al. Cell 2008, 134:577-86).

Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, in certain embodiments, siRNA target sites are selected at different positions along the length of the gene sequence. Finally, the potential target sites can be compared to the appropriate genome database. Any target sequences with more than 16-17 contiguous base pairs of homology to other coding sequences may be eliminated from consideration in certain cases.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., Proc. Natl. Acad. Sci. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., Nature Biotechnology 20:500-505, 2002).

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

One of the main concerns in siRNA targeting of selected cellular genes is the potential for off-target effects and the resulting possibility of uncontemplated toxicities due to the knockdown of important off-target cellular genes. In certain embodiments, 2'-O-Me derivatives of the siRNAs are used to minimize off-target effects.

In another embodiment, anti-IκBα or IκBα or anti-IκBε siRNAs are expressed predominantly in CD4$^+$ cell in a tissue-specific manner using either a tissue-specific regulatory element or an inducible regulatory element and tissue-specific induction. Examples of inducible regulatory elements include, but are not limited to, regulatory elements that responded to exogenous signals or stresses, such as heat, hormones, hypoxia, cytokines or metal ions, as well as artificial inducible systems such as the tetracycline inducible system; the FK506/rapamycin inducible system, the RU486/mifepristone inducible system, and the ecdysone inducible system.

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

Administration

The anti-IκBα agent, anti-IκBε agent and antiviral agent may be administered via commonly used administrative routes such as parenteral administration (e.g., intravenous, intramuscular, intraperitoneal, intradermal, and subcutaneous administration), enteral administration (e.g., oral and rectal administration), and topical administration (e.g., transdermal, inhalational, intranasal and vaginal administration). In one embodiment, the anti-IκBα agent and/or anti-IκBε agent are administered after the administration of the antiviral agent. In another embodiment, the anti-IκBα agent and/or anti-IκBε agent, are administered before the administration of the antiviral agent. In yet another embodiment, the anti-IκBα agent and/or anti-IκBε agent are administered concurrently with the administration of the antiviral agent.

Pharmaceutical Compositions

Another aspect of the present invention relates to a pharmaceutical composition for treating latent HIV infection. The pharmaceutical composition contains (1) an anti-IκBα agent, or an anti-IκBε agent or both, and (2) a pharmaceutically acceptable carrier.

The pharmaceutical composition may be administered prior to administration of an antiviral agent, concurrently with an antiviral agent, or alternatively with an antiviral agent. In one embodiment, the pharmaceutical composition further contains an anti-viral agent.

As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, dispersion media, coatings, antibacterial or antifungal agents, isotonic and absorption delaying agents, and the like, compatible with pharmaceutical administration. A pharmaceutically acceptable carrier may also include antibodies, including single chain antibodies, complexed with the anti-IkB agent, that may target the anti-IkB to particular cells types, other molecules, such as modified ligands for cellular receptors, capable of targeting the anti-IkB agent to particular cell types, and methods to encapsulate, complex, and otherwise protect and target the anti-IkB. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition is formulated to be compatible with its intended route of administration. Solutions or suspensions used for parenteral application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose; lipids, micelles, virions and pseudovirions. pH can be adjusted with acids or bases, such as hydrochloric acid or sodium hydroxide. The parenteral preparation can be enclosed in ampoules, disposable syringes or multiple dose vials made of glass or plastic.

In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

EXAMPLES

Example 1

Knockdown of GAPDH RNA in U1 Cells

U1 cell line is a well characterized and widely used latently infected cell line model, with a low background of spontaneous activation (see e.g., Tyagi, M. and J. Karn, 2007. Embo J 26:4985-95). In addition, U1 is a monocyte/macrophage-like line, which is representative of the HIV latently infected cell types that are thought to pose some of the most challenging HIV latent reservoirs, for example in potential sanctuary sites such as the CNS and reproductive tract.

Initial experiments were carried out in U1 cells to optimize transfection procedures using siRNAs against GAPDH. Greater than 90% knockdown of GAPDH RNA was achieved, as assessed by real time PCR.

Example 2

Knockdown of IκB RNA in U1 Cells

IκBα siRNAs (3'-GAACAUGGACUUGUAUAUU-5' (SEQ ID NO: 1), 3'-GGACGAGAAAGAUCAUUGA-5' (SEQ ID NO: 2), 3'-GGUAGGAUCAGCCCUCAUU-5' (SEQ ID NO: 3)); an IκBβ siRNA (3'-CCCGAGGGCGAG-GAUGAGAAA-5' (SEQ ID NO: 4)), IκBε siRNAs (3'-GGAAACUGCUGCUGUGUAC-5' (SEQ ID NO: 5), 3'-GGAAGGGAAGUUUCAGUAA-5' (SEQ ID NO: 6), 3'-GUACGACUCUGGCAUUGAG-5' (SEQ ID NO: 7), 3'-GAAUUGCUGCUUCGGAAUG-5' (SEQ ID NO: 8)), and a non-specific siRNA control pool (D-001206-14) were purchased from Dharmacon, Lafayette, Colo. The siRNAs were transfected into $1.5 \times 10^6$ U1 latently infected cells resuspended in 0.1 ml in the transfection cassette using an Amaxa Nucleofector with Nucleofector solution V and program W1 (Amaxa Inc., Gaithersburg, Md.). Concentrations varying from 62.5 nM to 2000 nM were tested to generate dose-response curves for the siRNA pools and individual siRNAs. After transfection, the cells were washed transferred to wells in a 6-well plate with medium. Samples were collected periodically for p24 assays of the supernatant and cells harvested for protein and RNA extraction. (The data shown in FIGS. 1-3 was obtained 72 h after transfection.). RNA was extracted with the Qiagen RNeasy mini kit and assayed for HIV p24 antigen with the Perkin-Elmer Alliance ELISA. Following RNA extraction, RNA concentrations were determined using a NANODROP® HD-1000 Spectrophotometer. Amounts of specific RNAs were determined by real time RT-PCR. Reverse transcription was primed with random hexamers and cDNA synthesized using SUPERSCRIPT™ II (Invitrogen) and SUPERASE-IN™ (Ambion). Taqman (Applied Biosystems) real time gene expression assays using the 7900HT Fast Real-Time instrument (Applied Biosystems) and ABI validated gene-specific Taqman probes. Changes in the amounts of specific gene RNAs were calculated with respect to changes observed when the cells were transfected with the non-specific siRNA pool.

To assess the potential toxicity on the cells of the siRNAs against the 3 major IκB species, IκBα, IκBβ, and IκBε, cell viability was determined using trypan blue exclusion (FIG. 1). Cells maintained greater 90% viability over 72 h, indicating that the siRNAs were relatively non-toxic, which suggests that targeting the IκBs with siRNA may be a viable approach to activating latent HIV.

Figure 2:
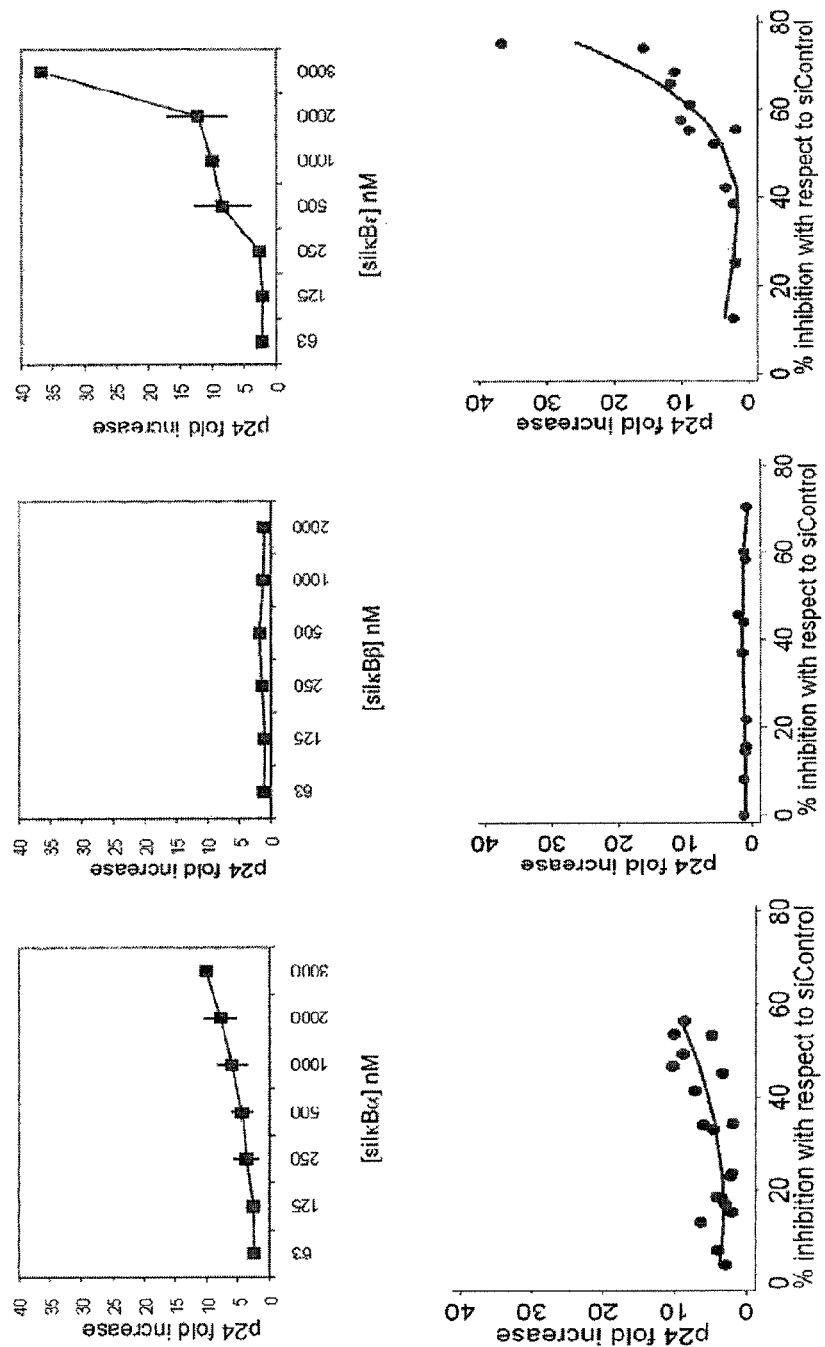
FIG. 2 is a composite of diagrams showing effects of siRNA against I$\kappa$B$\alpha$, I$\kappa$B$\beta$, and I$\kappa$B$\epsilon$ on expression of the I$\kappa$B RNAs and the production of p24 in U1 cells. Top Panels: siRNA against I$\kappa$B$\alpha$ (left panel), I$\kappa$B$\beta$ (middle panel), or I$\kappa$B$\epsilon$ (right panel) was transfected into U1 cells using an Amaxa Nucleofector and HIV p24 content in the cell supernatants was assayed by ELISA. Bottom panels: The data in the top panel is re-plotted to show HIV activation as a function of RNA knockdown.

To assess the potential ability of siRNAs against the major IκBs to activate HIV expression we conducted a dose-response preliminary HIV activation experiment using the siRNAs targeting the IκBs described above. Varying amounts of the siRNAs were transfected into the U1 cells. RNAs for the 3 major IκBs were assayed using the real time PCR assays described above and normalized to the results obtained with the non-specific siRNA. Supernatants were also collected from the cells at the same times and assayed for HIV p24 antigen by ELISA. The results were normalized and a fold-increase in p24 production calculated. Results of the experiment are shown in FIG. 2, The anti-IκBα produced at ~10-fold increase in p24 at the maximal concentration, while the anti-IκBβ had essentially no HIV-activating effect and the anti-IκBε produced an almost 40-fold activation. As shown in the bottom panels of FIG. 2. When is knocked down beyond about 60%, p24 production increases dramatically. IκBα knockdown starts to produce HIV activation beyond 50-60% inhibition. It is clear that even high degrees of IκBβ knockdown have no effect on the activation of HIV.

Figure 3:
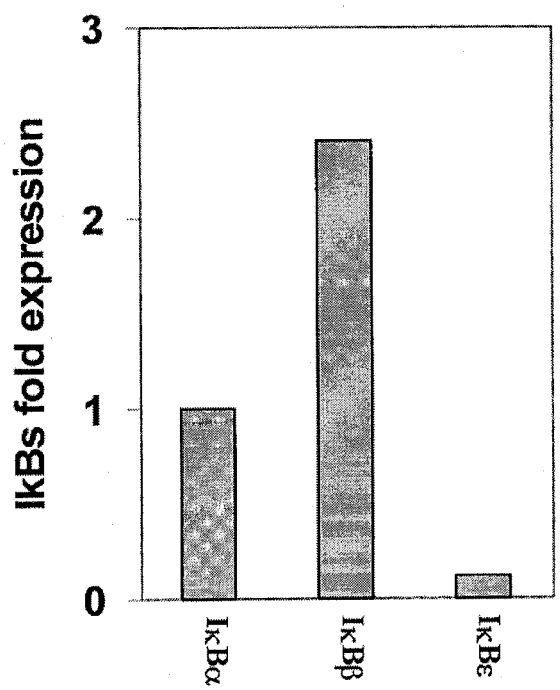
FIG. 3 is a diagram showing relative expression of I$\kappa$B$\alpha$, I$\kappa$B$\beta$, and I$\kappa$B$\epsilon$ in U1 cells. Real time RT-PCR Taqman assays for the IkBs were normalized to an internal GAPDH Taqman standard and then the values for IkB$\beta$ and IkB$\epsilon$ were compared to that for IkB$\tilde{a}$.

To better understand the differences in HIV activation observed when the 3 different IκBs were targeted for knockdown, the relative expression levels of IκBα, IκBβ and IκBε in U1 cells were compared. Each IκB was assayed normalized to an internal GAPDH control, and then IκBβ and IκBε were compared to IκBα. As shown in FIG. 3, cells contained ~2.4 fold more IκBβ than IκBα, and that the amount of IκBε was only ~0.125-fold that of IκBα. The relatively low amounts of IκBε may also help account for why knockdown of IκBε is more effective than knockdown of the others and provides further argument for its utility as a silencing target. The relatively higher amounts of IκBα and IκBβ particularly, may account for why it is more difficult to activate HIV by knocking down those RNAs.

The cross-talk among the different anti-IκB siRNAs used in these preliminary experiments was modest. Knocking down IκBα to 50% decreased IκBε 3% and IκBβ 29%. Knocking down IκBβ 78% had no effect on IκBα or IκBε. Knocking down IκBε to 74% had no effect on IκBα and decreased IκBβ 36%. The HIV-expression activating effect resulting from IκBε knockdown therefore appeared reasonably specific to IκBε, since knocking down IκBβ to even a relatively high degree had no HIV-activating effect.

Example 3

Synergistic Effects of IκBs on HIV Activation

Figure 4:
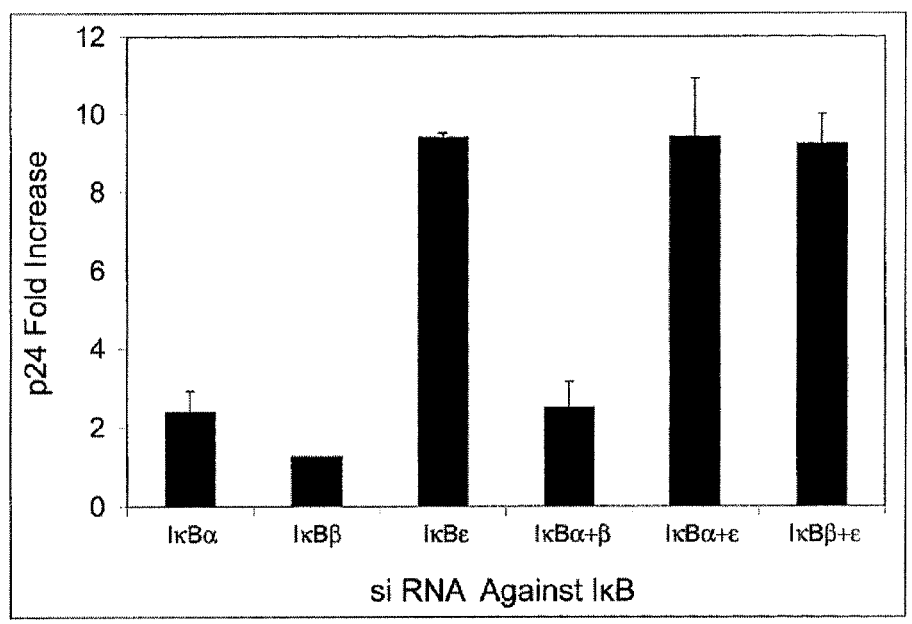
FIG. 4 is a diagram showing activation of HIV expression in U1 cells by siRNAs against I$\kappa$B$\alpha$, I$\kappa$B$\epsilon$, and I$\kappa$B$\epsilon$ alone and in pairwise combinations. I$\kappa$B$\epsilon$ effectively activates HIV expression by itself, with no apparent additive effects from the siRNAs against I$\kappa$B$\alpha$ or I$\kappa$B$\beta$. (Experiments were performed with siRNAs at 1000 nM).

To assess whether knocking down the different IκBs might have additive or synergistic effects on HIV activation, transfections of pairwise combinations of the siRNAs against the IκBs were conducted. The results of these experiments are shown in FIG. 4. The experiments confirm that the siRNAs against IκBα modestly activate HIV expression, the siRNAs against IκBβ have little to no effect on HIV activation, and the siRNA against IκBε strongly activated HIV expression. In the pairwise combinations, the activation produced by siRNAs against IκBα had minimal to no additive effects over the activation produced by the siRNA against IκBε. Overall, these results indicate that knocking down IκBε effectively activates HIV. Since IκBε does not appear to be essential for cellular function, and since siRNAs can be targeted to specific cell types, siRNAs against IκBε may offer an effective approach to attacking and depleting the latent reservoir of HIV infected cells.

Although various specific embodiments and examples have been described herein, those having ordinary skill in the art will understand that many different implementations of the invention can be achieved without departing from the spirit or scope of this disclosure.

What is claimed is:

1. A pharmaceutical composition for treating latent HIV infection, comprising:
   (1) an effective amount of an anti-IκBα agent, an anti-IκBε agent or both; and
   (2) a pharmaceutically acceptable carrier,
   wherein said anti-human IκBα agent and/or said anti-human IκBε agent are selected from the group consisting of iRNA agents, antisense RNA, vectors expressing iRNA agents and/or antisense RNA, PNA, anti-IκBα antibodies, anti-IκBε antibodies, and small molecules that target IκBα-NFκB and IκBε-NFκB interactions, wherein said anti-human IκBα agent or said anti-human IκBε agent reduces the level of IκBα or IκBε gene expression or a biological activity of the IκBα or IκB-ε protein in cells latently infected by HIV, resulting in activation of HIV expression in such cells.

2. The pharmaceutical composition of claim 1, wherein said anti-IκBα agent comprises an anti-IκBα siRNA and wherein said anti-IκBε agent comprises an anti-IκBε siRNA.

3. The pharmaceutical composition of claim 1, wherein said anti-IκBα agent is an agent capable of in vivo expression of an anti-IκBα siRNA and wherein said anti-IκBε agent is an agent capable of in vivo expression of an anti-IκBα siRNA.

4. The pharmaceutical composition of claim 1, wherein said anti-IκBα agent and/or anti-IκBε agent are formulated in liposomal particles.

5. The pharmaceutical composition of claim 1, further comprising an antibody or other ligand capable of binding a cell surface protein for specific cell targeting.

6. The pharmaceutical composition of claim 2, wherein said anti-IκBα siRNA comprises a sequence selected from the group consisting of SEQ ID NOS: 1-3, and wherein said anti-IκBε siRNA comprises a sequence selected from the group consisting of SEQ ID NOS: 5-8.

7. The pharmaceutical composition of claim 2, wherein said anti-IκBα siRNA comprises SEQ ID NO: 2, and wherein said anti-IκBε siRNA comprises SEQ ID NO: 6.

8. The pharmaceutical composition of claim 1, further comprising one or more anti-viral agents.

9. The pharmaceutical composition of claim 8, wherein said one or more antiviral agents are selected from the group consisting of reverse transcriptase inhibitors, protease inhibitors, HIV integration inhibitors, HIV entry inhibitors, viral maturation inhibitors, agents targeting the expression of HIV genes, agents targeting key host cell genes and gene products involved in HIV replication, and other anti-HIV agents, iRNA agents, antisense RNA, vectors expressing iRNA agents or antisense RNA, PNA and antiviral antibodies.

10. The pharmaceutical composition of claim 1, wherein said anti-human IκBα agent and/or said anti-human IκBε agent specifically target HIV host cells.

11. A method for treating HIV infection in humans, comprising:
    administering to a subject in need of such treatment an effective amount of an anti-human IκBα agent, an anti-human IκBε agent or both, wherein said anti-human IκBα agent and/or an anti-human IκBε agent are selected from the group consisting of iRNA agents, antisense RNA, vectors expressing iRNA agents or antisense RNA, PNA, anti- IκBα antibodies and anti-IκBε antibodies, and small molecules that target IκBα-NFκB and IκBε-NFκB interactions; and
    administering to said subject an effective amount of an antiviral agent selected from the group consisting of reverse transcriptase inhibitors, protease inhibitors, viral integration inhibitors, viral entry inhibitors, viral maturation inhibitors, iRNA agents, antisense RNA, vectors expressing iRNA agents or antisense RNA, PNA and antiviral antibodies.

12. The method of claim 11, wherein said anti-IκBα and/or anti-IκBε agents are PNA.

13. The method of claim 11, wherein said anti-IκBα agent comprises an anti-IκBα antibody.

14. The method of claim 11, wherein said anti-IκBε agent comprises an anti-IκBε antibody.

15. The method of claim 11, wherein said anti-IκBα and/or anti-IκBε agents comprise small molecules that target IκBα-NFεB and/or IκBε-NFκB interaction or stability.

16. The method of claim 11, wherein said anti-human IκBα agent and/or said anti-human IκBε agent target HIV host cells.

17. The pharmaceutical composition of claim 1, wherein said anti-human IκBα agent and/or said anti-human IκBε agent comprises an iRNA agent and/or antisense RNA.

18. The pharmaceutical composition of claim 1, wherein said anti-human IκBα agent and/or said anti-human IκBε agent comprises a PNA.

19. The pharmaceutical composition of claim 1, wherein said anti-human IκBα agent and/or said anti-human IκBε agent comprises an anti-IκBα antibody and/or an anti-IκBε antibody.

20. The pharmaceutical composition of claim 1, wherein said anti-human IκBα agent and/or said anti-human IκBε agent comprises a small molecule that targets IκBα-NFκB and/or IκBε-NFκB interactions.

* * * * *

SEQUENCE LISTING

<160> NUMBER OF SEQ ID NOS: 8

<210> SEQ ID NO 1
<211> LENGTH: 19
<212> TYPE: RNA
<213> ORGANISM: artificial
<220> FEATURE:
<223> OTHER INFORMATION: synthetic siRNA

<400> SEQUENCE: 1
gaacauggac uuguauauu                                                    19

<210> SEQ ID NO 2
<211> LENGTH: 19
<212> TYPE: RNA
<213> ORGANISM: artificial
<220> FEATURE:
<223> OTHER INFORMATION: synthetic siRNA

<400> SEQUENCE: 2
ggacgagaaa gaucauuga                                                    19

<210> SEQ ID NO 3
<211> LENGTH: 19
<212> TYPE: RNA
<213> ORGANISM: artificial
<220> FEATURE:
<223> OTHER INFORMATION: synthetic siRNA

<400> SEQUENCE: 3
gguaggauca gcccucauu                                                    19

<210> SEQ ID NO 4
<211> LENGTH: 21
<212> TYPE: RNA
<213> ORGANISM: artificial
<220> FEATURE:
<223> OTHER INFORMATION: synthetic siRNA

<400> SEQUENCE: 4
cccgagggcg aggaugagaa a                                                 21

<210> SEQ ID NO 5
<211> LENGTH: 19
<212> TYPE: RNA
<213> ORGANISM: artificial
<220> FEATURE:
<223> OTHER INFORMATION: synthetic siRNA

<400> SEQUENCE: 5
ggaaacugcu gcuguguac                                                    19

<210> SEQ ID NO 6
<211> LENGTH: 19
<212> TYPE: RNA
<213> ORGANISM: artificial
<220> FEATURE:
<223> OTHER INFORMATION: synthetic siRNA

<400> SEQUENCE: 6
ggaagggaag uuucaguaa                                                    19

<210> SEQ ID NO 7
<211> LENGTH: 19
<212> TYPE: RNA

```
<213> ORGANISM: artificial
<220> FEATURE:
<223> OTHER INFORMATION: synthetic siRNA

<400> SEQUENCE: 7
guacgacucu ggcauugag                                                   19

<210> SEQ ID NO 8
<211> LENGTH: 19
<212> TYPE: RNA
<213> ORGANISM: artificial
<220> FEATURE:
<223> OTHER INFORMATION: synthetic siRNA

<400> SEQUENCE: 8
gaauugcugc uucggaaug                                                   19
```